United States Patent
Nagira et al.

(10) Patent No.: US 10,550,399 B2
(45) Date of Patent: Feb. 4, 2020

(54) PLANT TRANSFORMATION METHOD USING PLANT GROWTH INHIBITING HORMONE

(71) Applicant: KANEKA CORPORATION, Osaka-shi (JP)

(72) Inventors: Yozo Nagira, Takasago (JP); Ryozo Imai, Sapporo (JP); Kentaro Sasaki, Sapporo (JP); Naoaki Taoka, Takasago (JP); Keiji Matsumoto, Takasago (JP); Masahiro Nogawa, Ueda (JP); Mineo Kojima, Nagoya (JP)

(73) Assignee: KANEKA CORPORATION, Osaka-shi (JP)

( * ) Notice: Subject to any disclaimer, the term of this patent is extended or adjusted under 35 U.S.C. 154(b) by 218 days.

(21) Appl. No.: 14/404,532

(22) PCT Filed: May 31, 2013

(86) PCT No.: PCT/JP2013/065764
§ 371 (c)(1),
(2) Date: Nov. 28, 2014

(87) PCT Pub. No.: WO2013/180311
PCT Pub. Date: Dec. 5, 2013

(65) Prior Publication Data
US 2015/0218570 A1 Aug. 6, 2015

(30) Foreign Application Priority Data
May 31, 2012 (JP) .................. 2012-124467

(51) Int. Cl.
*C12N 15/82* (2006.01)
(52) U.S. Cl.
CPC ............... *C12N 15/8205* (2013.01)
(58) Field of Classification Search
None
See application file for complete search history.

(56) References Cited

U.S. PATENT DOCUMENTS

| | | | |
|---|---|---|---|
| 6,162,965 A | 12/2000 | Hansen | |
| 2008/0229447 A1* | 9/2008 | Hwang | A01H 4/005 800/279 |
| 2011/0030101 A1 | 2/2011 | Ishida et al. | |
| 2013/0125265 A1 | 5/2013 | Ishida et al. | |

FOREIGN PATENT DOCUMENTS

| | | |
|---|---|---|
| JP | 2002534129 | 10/2002 |
| JP | 2010-161989 | 7/2010 |
| JP | 2010161989 | * 7/2010 |
| JP | 2010538670 | 12/2010 |
| WO | WO 2005/024034 A1 | 3/2005 |
| WO | WO 2008/119136 A1 | 10/2008 |
| WO | WO 2012/015039 | 2/2012 |

OTHER PUBLICATIONS

Kagaya et al (Abscisic Acid—Induced Transcription Is Mediated by Phosphorylation of an Abscisic Acid Response Element Binding Factor, TRAB1. The Plant Cell, vol. 14, 3177-3189, Dec. 2002).*
Werner et al (Regulation of plant growth by cytokinin. PNAS, 98 (18) 10487-10492, 2001).*
Razzaq et al (Development of in planta transformation protocol for Wheat. African Journal of Biotechnology vol. 10(5), pp. 740-750, Jan. 31, 2011).*
Vetten et al (A transformation method for obtaining marker-free plants of a cross-pollinating and vegetatively propagated crop. Nature biotechnology. vol. 21: 439-442, Apr. 2003).*
Ella et al (Effect of Abscisic Acid and Zeatin on Plant Regeneration from Scutellum-derived Callus of Rice (*Oryza sativa* L. Cv. 'Nona Bokra'). Philipp /. Crop Sci. 16(1): 3-6, 1991).*
Dodd (Abscisic acid and stomatal closure: a hydraulic conductance conundrum? New Phytologist 197: 6-8, 2013) (Year: 2013).*
Fan et al (Exogenous abscisic acid application decreases cadmium accumulation in *Arabidopsis* plants, which is associated with the inhibition of IRT1-mediated cadmium uptake. Frontiers in Plant Science. 5:p. 1-8, 2014) (Year: 2014).*
Sun et al (Crosstalk between jasmonic acid, ethylene and Nod factor signaling allows integration of diverse inputs for regulation of nodulation. The Plant Journal 46, 961-970, 2006) (Year: 2006).*
International Search Report dated Jul. 2, 2013 in corresponding PCT/JP2013/065764.
Mineo Kojima, et al., "Development of Versatile, Simple, and Highly Efficient in-planta Transformation Method", Seibutsu-kogaku kaishi (Journal of the Society for Biotechnology, Japan), vol. 85, 2007, No. 2, pp. 57-62, (with English translation).
Jon Isaksson, et al., "Extracellular enzymes of Erwinia carotovora eliminate the need for Azacytidine treatment for high frequency transformation of *Arabidopsis thaliana*", In Vitro Cellular & Developmental Biology Plant, 1998, vol. 34, No. 1 pp. 41-45.
Extended Search Report dated Nov. 11, 2015 in European Patent Application No. 13796736.0.

(Continued)

*Primary Examiner* — Medina A Ibrahim
*Assistant Examiner* — Wayne Zhong
(74) *Attorney, Agent, or Firm* — Oblon, McClelland, Maier & Neustadt, L.L.P.

(57) ABSTRACT

This invention provides a method of plant transformation via *Agrobacterium* comprising inoculating and infecting a plant with an *Agrobacterium* carrying a foreign-gene-containing vector under application of a plant growth-inhibiting hormone. This invention also provides a method of plant transformation via *Agrobacterium* comprising transforming a plant with an *Agrobacterium* carrying a vector comprising a T-DNA region in which a foreign gene is contained but no selectable marker gene is contained.

3 Claims, 6 Drawing Sheets
Specification includes a Sequence Listing.

(56) References Cited

OTHER PUBLICATIONS

Ming Cheng, et al., "Desiccation of plant tissues post-agrobacterium infection enhances T-DNA delivery and increases stable transformation efficiency in wheat", in Vitro Cell. Dev. Biol.—Plant 39, Nov.-Dec. 2003, 2003 Society for in Vitro Biology, pp. 595-604.
Office Action dated Mar. 28, 2017, in Japanese patent application No. 2013-114844.
Zuniga et al, "Hydroxamic acid content in undifferentiated and differentiated tissues of wheat", *Phytochemistry*, 1991, vol. 30, No. 10, pp. 3281-3283.
Intention to Grant European patent application No. 13796736.0, dated Dec. 6, 2017 (7 pages).
Supartana et al, "Development of Simple and Efficient in *Planta* Transformation Method for Wheat (*Triticum aestivum* L.) Using *Agrobacterium tumefaciens*", *Journal of Bioscience and Bioengineering*, 2006, vol. 102, No. 3, pp. 162-170.
Aragao et al, Selection of transgenic meristematic cells utilizing a herbicidal molecule results in the recovery of fertile transgenic soybean [*Glycine max* (L.) Merril] plants at high frequency, *Theor Appl Genet*, (2000), vol. 101, pp. 1-6.
Khalafalla et al, "Optimization of Particle Bombardment Conditions by Monitoring of Transient sGFP(S65T) Expression in Transformed Soybean", *Breeding Science*, (2005), vol. 55, pp. 257-263.
Kim et al, "Isolation of Stress-Related Genes of Rubber Particles and Latex in Fig Tree (*Ficus carica*) and their Expressions by Abiotic Stress or Plant Hormone Treatments", *Plant Cell Physiol.* (2003), vol. 44, No. 4, pp. 412-419 JSPP © 2003.
Myers et al, "Abscisic Acid Inhibition of Endosperm Cell Division in Cultured Maize Kernels", *Plant Physiol.l*, (1990) vol. 94, pp. 1330-1336.
Tungngoen et al, "Hormonal treatment of the bark of rubber trees (*Hevea brasiliensis*) increases latex yield through latex dilution in relation with the differential expression of two aquaporin genes", *Journal of Plant Physiology*, (2011), vol. 168, pp. 253-262.
Veisseire et al, "Effect of abscisic acid and cytokinins on the development of somatic embryos in *Hevea brasiliensis*", *Plant Cell, Tissue and Organ Culture*, (1994), vol. 39, pp. 219-220.
Walton et al, "The Effects of Abscisic Acid on Growth and Nucleic Acid Synthesis in Excised Embryonic Bean Axes", *Plant Physiol*, (1970), vo. 45, pp. 37-40.

* cited by examiner

Fig. 2

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
acctcgcatt acccttacgc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tatccacgcc gtattcggtg                                              20
```

PLANT TRANSFORMATION METHOD USING PLANT GROWTH INHIBITING HORMONE

TECHNICAL FIELD

The present invention relates to a plant transformation method with improved transformation efficiency.

BACKGROUND ART

At present, general plant transformation is carried out via direct introduction of a foreign gene into a callus or a piece of tissue in an in vitro culture system via *Agrobacterium tumefaciens* or by particle bombardment. However, such techniques are insufficient in terms of transformation efficiency, and thus requires marker selection through the introduction of a selectable marker gene. In contrast, expression of a selectable marker gene may influence the phenotype of a resulting transformed plant, and it is preferable from the viewpoint of safety that a transformed plant does not comprise a selectable marker gene. Accordingly, development of transformed plants without the introduction of selectable marker genes is desired.

A floral-dip method by which plant transformation is carried out without the use of a callus or a piece of tissue in an in vitro culture system has been known as a technique for transformation of *Arabidopsis thaliana*. Because of low transformation efficiency, however, there have been substantially no reports of application of such technique to other plant species. Patent Document 1 and Non-Patent Document 1 disclose versatile methods of in planta transformation that enable transformation via the in planta method without in vitro culture of plant cells. However, such techniques remain problematic in terms of transformation efficiency.

REFERENCES

Patent Documents

Patent Document 1: International Publication WO 2005/024034

Non-Patent Documents

Non-Patent Document 1: Kojima et al., the Journal of Bioscience and Bioengineering, Vol. 85, No. 2, p. 57-62 (2007)

SUMMARY OF THE INVENTION

Problem to be Solved by Invention

It is an object of the present invention to provide an improved method of plant transformation. It is another object of the present invention to provide a method of plant transformation without the introduction of a selectable marker gene. It is a further object of the present invention to provide a method of plant transformation with improved efficiency.

Means for Solving the Problem

The present inventors have conducted concentrated studies in order to solve the above problems. As a result, they discovered that a plant growth-inhibiting hormone would increase the transformation efficiency of a method of plant transformation via *Agrobacterium*. They also discovered a method for transforming a plant without the introduction of a selectable marker gene by such increased transformation efficiency. This has led to the completion of the present invention.

Specifically, the present invention includes the followings.

[1] A method of plant transformation via *Agrobacterium* comprising inoculating and infecting a plant with an *Agrobacterium* carrying a foreign-gene-containing vector under application of a plant growth-inhibiting hormone.

[2] The method according to above [1], wherein the plant growth-inhibiting hormone is environmental stress-inducible.

[3] The method according to above [1] or [2], wherein the plant growth-inhibiting hormone is abscisic acid or jasmonic acid.

[4] A method of plant transformation via *Agrobacterium* comprising transforming a plant with an *Agrobacterium* carrying a vector comprising a T-DNA region in which a foreign gene is contained but no selectable marker gene is contained.

[5] The method according to any of above [1] to [4], wherein the method of plant transformation via *Agrobacterium* is a method of in-planta transformation comprising inoculating an *Agrobacterium* into a wound site of a meristem.

[6] The method according to above [5], wherein the *Agrobacterium* is inoculated into a wound site of a meristem of a seed embryo.

[7] The method according to above [6], wherein the seed has a shoot with a length of 1 mm or less.

[8] The method according to any of above [1] to [7], which comprises subjecting the plant inoculated with the *Agrobacterium* to vacuum treatment and/or co-culture.

[9] The method according to any of above [1] to [8], wherein the plant is a Poaceae or Leguminosae plant.

[10] A medium for preparing *Agrobacterium* used for plant transformation, which contains a plant growth-inhibiting hormone.

This description includes the disclosure of Japanese Patent Application No. 2012-124467, to which the present application claims priority.

Effects of the Invention

According to the method of the present invention, plant transformation via *Agrobacterium* can be carried out with improved efficiency. In one embodiment of the present invention, transformation efficiency of the method of plant transformation via *Agrobacterium* can be significantly improved. In another embodiment of the present invention, plant transformation can be carried out without the introduction of a selectable marker gene.

BRIEF DESCRIPTION OF THE DRAWINGS

FIG. 2A shows results for the T0 generation and FIG. 2B shows results for the T1 generation.

FIG. 3A shows an untransformant, and FIG. 3B shows a transformant (T1 generation).

FIG. 4A shows an untransformant, and FIG. 4B shows a transformant (T1 generation).

EMBODIMENTS FOR CARRYING OUT THE INVENTION

Hereafter, the present invention is described in detail.

The present invention relates to an improved method of plant transformation via *Agrobacterium*. The present invention relates to a method of plant transformation via *Agrobacterium* comprising inoculating a plant with an *Agrobacterium* under application of a plant growth-inhibiting hormone. According to the method of the present invention, plant transformation efficiency can be improved by applying a plant growth-inhibiting hormone during the inoculation of a plant with an *Agrobacterium*.

In a more specific embodiment of the method of plant transformation via *Agrobacterium* of the present invention, a plant can be inoculated and infected using an *Agrobacterium* carrying a foreign-gene-containing vector supplemented with a plant growth-inhibiting hormone, thereby introducing a foreign gene into a plant genome and accomplishing a high efficient plant transformation.

The present invention also relates to a method of transforming a plant, characterized in that a plant is transformed with an *Agrobacterium* carrying a vector containing no selectable marker gene in the T-DNA region, in a plant transformation via *Agrobacterium*. This method of plant transformation is preferably carried out using the method for improving plant transformation efficiency as described above.

The "method of plant transformation via *Agrobacterium*" underlying the method of the present invention is generally referred to as an *Agrobacterium*-mediated transformation method or an *Agrobacterium* method. This is a method for transforming a plant by introducing a foreign gene into a plant cell genome via *Agrobacterium*. *Agrobacterium* enables the insertion of a T-DNA region of a vector such as a plasmid carried by *Agrobacterium* into a plant chromosomal DNA, in a plant cell infected with the *Agrobacterium*. In the method of plant transformation via *Agrobacterium*, a vector (preferably, a binary vector) into which a foreign gene to be introduced into a plant has been incorporated under the control of a promoter and a terminator located between the right border sequence (RB) and the left border sequence (LB) of the T-DNA region is introduced into an *Agrobacterium* by a conventional technique, and a plant is inoculated and infected with the *Agrobacterium*, so that the foreign gene in the T-DNA region can be introduced into the plant.

More specifically, for example, a transformation method comprising infecting a plant callus or a piece of tissue in an in vitro culture system with an *Agrobacterium* to introduce a foreign gene and regenerating it to a plant body via in vitro culture, thereby preparing a transformed plant, may be employed as the method of plant transformation via *Agrobacterium* in the present invention. Alternatively, a method of in planta transformation referred to as a floral dip method that is generally used for *Arabidopsis thaliana* may be employed in the present invention. In the method of the present invention, further, a method of in planta transformation comprising inoculating and infecting a meristem of a plant individual (a plant body or seed) with an *Agrobacterium* strain carrying a foreign-gene-containing vector can be more preferably employed as the method of plant transformation via *Agrobacterium*.

In one embodiment, the method of the present invention is characterized in that, in the method of plant transformation via *Agrobacterium*, in particular, plant transformation is carried out with an *Agrobacterium* that carries a vector comprising a T-DNA region in which a foreign gene is contained but no selectable marker gene is contained (that is, a vector comprising a foreign gene introduced into a T-DNA region, into which no selectable marker gene has been introduced into the T-DNA region). A "foreign gene" within the T-DNA region used in this embodiment is not a selectable marker gene. The definition and specific examples of the term "selectable marker gene" are given below. In this method of the present invention, a transformed plant can be selected by detecting a foreign gene introduced into the genome or a nucleic acid such as mRNA or a protein expressed therefrom, without introducing a selectable marker gene, which is commonly used for selection of a transformant, into the genome of a host plant cell together with a foreign gene. For example, a transformant can be selected by amplifying at least a part of a foreign gene in the genome by PCR and detecting an amplified fragment of interest. Since resulting transformed plants do not contain any selectable marker gene, they would not be selected with the use of a selectable marker (e.g., via selection based on antibiotic resistance or herbicide resistance). This method may be carried out in combination with a method of *Agrobacterium* transformation with high transformation efficiency (e.g., the method described below), so that a transformant can be efficiently obtained without the introduction of a selectable marker gene into the genome of a plant host.

In another embodiment, the method of plant transformation via *Agrobacterium* of the present invention is characterized in that, in particular, a plant is inoculated with an *Agrobacterium* under application of a plant growth-inhibiting hormone. In the context of the present invention, "inoculating a plant with an *Agrobacterium* under application of a plant growth-inhibiting hormone" is artificial application of a plant growth-inhibiting hormone to a plant, so that a plant growth-inhibiting hormone is present at an inoculation site when inoculating a plant with an *Agrobacterium*. In one specific embodiment of inoculation of a plant with an *Agrobacterium* under application of a plant growth-inhibiting hormone, for example, a plant may be inoculated with an *Agrobacterium* solution supplemented with a plant growth-inhibiting hormone. In another embodiment, for example, a plant growth-inhibiting hormone is applied or added to the inoculation site, and then an *Agrobacterium* solution may be applied thereto, and this procedure may be carried out in a reverse order. Alternatively, a plant may be soaked in an *Agrobacterium* solution, and a plant growth-inhibiting hormone may be added thereto. It should be noted that inoculation of a plant with an *Agrobacterium* under application of a plant growth-inhibiting hormone is not limited to the embodiments described above.

A plant growth-inhibiting hormone used in the present invention is preferably environmental stress-inducible. The term "environmental stress-inducible" means that expression of the hormone is induced by environmental stress, such as drying stress, salt stress, or heavy metal stress, in a naturally occurring plant host. Preferred examples of environmental stress-inducible, plant growth-inhibiting hormones include, but are not limited to, plant hormones such as abscisic acid, jasmonic acid, ethylene, and salicylic acid.

The concentration of a plant growth-inhibiting hormone to be applied to a plant is not limited, provided that it exhibits inhibitory effects on plant growth. For example, the concentration of a plant growth-inhibiting hormone is preferably 1 to 1,000 µM, more preferably 5 to 500 µM, and further preferably 10 to 300 µM, at the final concentration when applied to a plant.

According to the present invention, transformation efficiency can be improved by inoculating a plant with an *Agrobacterium* under application of a plant growth-inhibiting hormone. This is considered because plant growth is inhibited through the action of a plant growth-inhibiting hormone, thereby *Agrobacterium* growth becomes predominant, and as a result, *Agrobacterium* infection is accelerated.

The *Agrobacterium* solution used for inoculating a plant under application of a plant growth-inhibiting hormone may further contain a surfactant, such as Tween 20. The *Agrobacterium* solution may contain a phenol, such as acetosyringone. These components can further improve transformation efficiency.

The method of plant transformation according to the present invention can be applied to any plants that can be infected with *Agrobacterium*. The method of plant transformation according to the present invention can be applied to dicotyledonous or monocotyledonous plants. Examples of plants to which the method of the present invention can be applied include, but not limited to: plants of Poaceae, such as wheat (*Triticum aestivum* L.), rice (*Oryza sativa*), barley (*Hordeum vulgare* L.), maize (*Zea mays* L.), sorghum (*Sorghum bicolor* L. Moench), Erianthus (*Erianthus* spp), guinea grass (*Panicum maximum* Jacq.), Miscanthus (*Miscanthus* spp), sugar cane (*Saccharum officinarum* L.), napier grass (*Pennisetum purpureum* Schumach), pampas grass (*Cortaderia argentea* Stapf), perennial ryegrass (*Lolium perenne* L.), Italian ryegrass (*Lolium multiflorum* Lam.), meadow-fescue (*Festuca pratensis* Huds.), tall fescue (*Festuca arundinacea* Schreb.), orchard grass (*Dactylis glomerata* L.), and timothy grass (*Phleum pratense* L.); plants of Leguminosae, such as soybean (*Glycine max*), azuki bean (*Vigna angularis* Wald.), common bean (*Phaseolus vulgaris* L.), and *faba* bean (*Vicia faba* L.); plants of Malvaceae, such as cotton (*Gossypium* spp.), kenaf (*Hibiscus cannabinus*), and okra (*Abelmoschus esculentus*); plants of Solanaceae, such as eggplant (*Solanum melongena* L.), tomato (*Solanum lycopersicum*), green pepper (*Capsicum annuum* L. var. *angulosum* Mill.), chilli pepper (*Capsicum annuum* L.), and tabacco (*Nicotiana tabacum* L.); plants of Brassicaceae, such as Mousear Cress (*Arabidopsis thaliana*), field mustard (*Brassica campestris* L.), napa (*Brassica pekinensis* Rupr), cabbage (*Brassica oleracea* L. var. *capitata* L.), radish (*Raphanus sativus* L.), and oilseed rape (*Brassica campestris* L., *B. napus* L.); plants of Cucurbitaceae, such as cucumber (*Cucumis sativus* L.), melon (*Cucumis melo* L.), watermelon (*Citrullus vulgaris* Schrad.), pumpkin (*C. moschata* Duch., *C. maxima* Duch.); plants of Convolvulaceae, such as sweet potato (*Ipomoea batatas*); plants of Liliaceae, such as welsh onion (*Allium fistulosum* L.), onion (*Allium cepa* L.), Chinese chive (*Allium tuberosum* Rottl.), garlic (*Allium sativum* L.), and asparagus (*Asparagus officinalis* L.); plants of Labiatae, such as perilla (*Perilla frutescens* Britt. var. *crispa*); plants of Compositae, such as chrysanthemum (*Chrysanthemum morifolium*), garland chrysanthemum. (*Chrysanthemum coronarium* L.), and lettuce (*Lactuca sativa* L. var *capitata* L.); plants of Rosaceae, such as rose (*Rose hybrida* Hort.) and strawberry (*Fragaria x ananassa* Duch.); plants of Rutaceae, such as satsuma mandarin (*Citras unshiu*) and Japanese pepper (*Zanthoxylum piperitum* DC.); plants of Myrtaceae, such as eucalyptus (*Eucalyptus globulus* Labill); plants of Salicaceae, such as poplar (*Populas nigra* L. var *italica* Koehne); plants of Chenopodiaceae, such as spinach (*Spinacia oleracea* L.) and sugar beet (*Beta vulgaris* L.); plants of Gentianaceae, such as gentian (*Gentiana scabra* Bunge var. *buergeri* Maxim.); and plants of Caryophyllaceae, such as carnation (*Dianthus caryophyllus* L.). Plants having low efficiency of gene introduction by a conventional transformation technique, such as Poaceae, Leguminosae and Malvaceae are particularly preferred as a target of the method of transformation according to the present invention.

*Agrobacterium* used in the method of the present invention is a *Rhizobium* plant pathogenic bacterium capable of causing *Agrobacterium*-mediated transformation. Examples of *Agrobacterium* include, but are not particularly limited to, *Agrobacterium tumefaciens, Agrobacterium vitis, Agrobacterium rhizogenes*, and *Agrobacterium radiobacter*. Specific examples include, but not limited to, *Agrobacterium tumefaciens* LBA4404, C58, EHA101, and A208 stains; *Agrobacterium vitis* F2/5 and S4 stains; *Agrobacterium rhizogenes* A4 and LBA9402 strains; and derivative strains thereof (e.g., an M21 mutant). *Agrobacterium* to be used in the method of the present invention may carry a Ti plasmid that lacks the tryptophan monooxygenase gene or has a disrupted tryptophan monooxygenase gene through, for example, insertion of a transposon so that its gene function has been lost. An example of such *Agrobacterium* is an M21 variant. *Agrobacterium* used in the method of the present invention preferably has a vir gene involved in gene introduction into a plant chromosomal DNA in its genome or a helper plasmid. *Agrobacterium* used in the method of the present invention more preferably comprises a helper plasmid having a vir gene involved in gene introduction into a plant cell and a foreign-gene-containing vector.

*Agrobacterium* carrying a foreign-gene-containing vector can be prepared by introducing a foreign gene to be introduced into a plant into the T-DNA region of a vector comprising the T-DNA region to prepare a foreign-gene-containing vector, and introducing the resulting vector into an *Agrobacterium*. The vector comprising the T-DNA region is a vector that is autonomously replicable in *Agrobacterium*, comprising a T-DNA region derived from an *Agrobacterium* plasmid; that is, a nucleotide sequence sandwiched between the right border sequence (RB) and the left border sequence (LB), and a replication origin. Preferably, the vector comprising the T-DNA region comprises a promoter and a terminator between the RB sequence and the LB sequence. It is more preferred that the vector comprising the T-DNA region be a binary vector that also comprises a replication origin of other microorganisms such as *E. coli* and yeast and is also autonomously replicable in the microorganism as well as *Agrobacterium*. The vector comprising the T-DNA region may comprise a vir gene outside the T-DNA region. Many vectors comprising the T-DNA regions for plant transformation that are suitable for foreign gene introduction are commercially available. Examples of the vectors comprising the T-DNA regions include, but are not limited to, pIG121-Hm, pRI909, pRI910, pBIN, pGA, SEV, pEND4K, pBI, pCIB10, pMRK63, pGPTV, pCGN1547, pART, pGKB5, pMJD80, pMJD81, pPZP, pBINPLUS, pRT100, BIBAC, pGreen, pCB, pPZP-RCS2, pMDC, pRCS2, and pORE and the like.

In one preferred embodiment of the present invention, a vector into which a foreign gene has been introduced in the T-DNA region (i.e., a foreign-gene-containing vector) may comprise a selectable marker gene outside the T-DNA region, but preferably does not comprise a selectable marker gene in the T-DNA region. In the context of the present invention, the term "selectable marker gene" refers to a gene that can provide a marker (label) that facilitates selection for a successfully transformed cell. Examples thereof include a gene that selectively imparts viability to a transformed cell under given conditions so as to enable selection of a transformed cell (e.g., a drug resistance gene and an auxotrophic complementary gene), a fluorescent protein gene, and an enzyme gene that catalyzes color reaction. Examples of selectable marker genes include, but are not limited to, kanamycin resistance gene, hygromycin resistance gene, phosphinothricin resistance gene, bialaphos resistance gene, gentamicin resistance gene, sulfonylurea resistance gene, dihydrofolate reductase gene, bleomycin resistance gene, luciferase gene, β-galactosidase gene, β-glucuronidase gene, and green fluorescent protein (GFP) gene. When the foreign-gene-containing vector does not comprise a selectable marker gene in the T-DNA region, no selectable marker gene would be introduced into a transformed plant. Thus, a transformed plant with higher trait stability and higher safety can be obtained. Transformation efficiency of the method of the present invention is significantly improved, and therefore a transformed plant can be selected with a sufficient efficiency via genome PCR or other means, without the introduction of a selectable marker gene and without using phenotype changes caused by the expression of a selectable marker gene as an indicator.

A foreign gene to be incorporated into the vector comprising the T-DNA region is any gene intended to be induced to express in a plant. The foreign gene may be a gene from a plant or animal. The term "foreign gene" refers to a nucleic acid (DNA, in general) that is exogenously introduced into a plant via *Agrobacterium*. For example, the foreign gene may be isolated from a host plant that is an intended target of gene introduction or a plant of the same species or strain as the host plant. In the context of the present invention, the "foreign gene" may encode a protein or functional RNA. Examples of the foreign genes include, but are not limited to, genes involved in increase of seed yield, environmental stress tolerance, such as low temperature, drying, salt, virus, disease, or high temperature tolerance; enhanced photosynthetic capacity, biomass production, or useful material production. Preferably, the foreign gene is not a selectable marker gene.

A foreign-gene-containing vector can be introduced into an *Agrobacterium* by a conventional technique. For example, a foreign-gene-containing vector can be introduced into an *Agrobacterium* by freeze-thawing or particle bombardment. An example of freeze-thawing is briefly described. Competent *Agrobacterium* cells are mixed with a foreign-gene-containing vector, incubated on ice for 5 minutes, frozen in liquid nitrogen for 5 minutes, incubated at 37° C. for 5 minutes, thawed, and then subjected to shake culture at room temperature or at 28° C. for 2 to 4 hours. The resulting culture is then cultured in an antibiotic-containing medium, and the formed single clones can be collected.

The resulting *Agrobacterium* carrying a foreign-gene-containing vector is preferably inoculated into a plant under application of a plant growth-inhibiting hormone, as described above. Inoculation of *Agrobacterium* may be carried out in accordance with a conventional technique. If the in planta transformation technique is employed in the present invention, it is preferred that a meristem of a plant individual (a plant body or seed) be inoculated with an *Agrobacterium* carrying a foreign-gene-containing vector. Any meristem of a plant can serve as an inoculation site. For example, a meristem of a shoot apex or axillary bud of a juvenile plant or seedling, or a meristem of a seed embryo is preferably inoculated. Alternatively, a flower meristem, such as the inflorescence meristem or the floral meristem, including a flower bud meristem, may be inoculated with an *Agrobacterium*. In the case of Poaceae plants, for example, a meristem of a seed embryo is preferably inoculated. Inoculation into a meristem of a seed embryo can be inoculation into a meristem of a shoot germinated from a seed (i.e., a stem or leaf, and typically a shoot apex), a meristem around the shoot (i.e., an embryonic portion around the shoot base), or a meristem of a root (typically, a root apex).

Inoculation into a meristem is preferably carried out for a wound site of the meristem. The wound site may be prepared by, for example, piercing the meristem with a sterilized needle (in general, the diameter is 0.01 to 1 mm, such as 0.20 to 0.71 mm) at several sites. The piercing depth can be, but not limited to, about 0.5 mm to 2 mm, such as 0.5 mm to 1.5 mm or 0.5 mm to 1 mm. Alternatively, other wounds may be made on the meristem, for example, a minimal cut or scratch. Wounds may be first made and the wound site may then be inoculated with an *Agrobacterium*. Alternatively, a plant may be first inoculated with an *Agrobacterium*, and then a wound may be made on the inoculation site.

If a plant is inoculated at the meristem of a seed embryo, it is preferred that a seed at the growth stage in which a shoot is not fully extended (i.e., a seed having an immature shoot) be used. The length of such a shoot of a seed varies to some extent depending on plant type, but typically, a seed with a shoot having a length of 2 mm or less, and preferably 1 mm or less, e.g., 0.5 mm to 1 mm can be advantageously used. The meristem of the seed at the growth stage, which has a shoot that has not yet been fully extended, can be easily and adequately wounded, which further facilitates the infection of *Agrobacterium*. In order to accelerate germination of such seed, a seed germinated via water absorption in advance can be used.

A plant inoculated with an *Agrobacterium* is preferably allowed to stand while in contact with a bacterial solution for a given period of time. For example, a seed inoculated with an *Agrobacterium* through soaking in an *Agrobacterium* solution (bacterial solution) remains soaked in the bacterial solution for 5 minutes to 2 hours, and preferably 10 minutes to 40 minutes. At this stage, the plant inoculated with *Agrobacterium* may be subjected to vacuum treatment. The vacuum treatment can facilitate *Agrobacterium* infection. The vacuum treatment can be carried out by, for example, reducing a pressure with an aspirator. The duration of the treatment may be the same as or shorter than the duration of the bacterial contact as described above.

The plant inoculated with *Agrobacterium* may be co-cultured with the *Agrobacterium*, so as to facilitate infection with *Agrobacterium*. In the method of the present invention, co-culture is preferably carried out at 15° C. to 30° C., more preferably at 20° C. to 30° C., and further preferably at 22° C. to 28° C. Co-culture may be carried out for a general period of time, and for example, for 12 hours to 10 days, preferably 24 hours to 5 days, and more preferably 36 hours to 4 days. By performing the co-culture at the temperatures, the growth of *Agrobacterium* can be facilitated, and *Agrobacterium* infection can be facilitated.

Either or both vacuum treatment and co-culture may be performed.

The plant inoculated with *Agrobacterium* may be subjected to disinfection of *Agrobacterium*, after infection. Disinfection can be carried out by, for example, treating the plant with an antibiotic, such as cefotaxime.

A plant infected with *Agrobacterium* and optionally disinfected, is cultivated to grow under adequate cultivation conditions. When the plant reaches a given growth stage, whether the introduced foreign gene has been incorporated into the genome is preferably verified via genome PCR or other means. A plant in which foreign gene introduction is confirmed is selected as a transformed plant and used as a plant of the T0 generation.

A plant of the T0 generation is allowed to form buds and cross to produce seeds. A plant thus obtained is a plant of the T1 generation. By verifying the incorporation of the foreign gene into the genome of the plant of the T1 generation, a stably transformed plant can be selected and obtained. For example, the incorporation of the foreign gene into the genome can be verified by performing genome PCR using the genomic nucleic acid as a template to amplify a part of or the entire region of the foreign gene, and detecting an amplified fragment of interest derived from the foreign gene.

Transformation efficiency for the transformed plant thus obtained can be determined. Transformation efficiency (T0 generation×T1 generation) is determined by multiplying transformation efficiency for the T0 generation (the number of transformed plants of T0 generation/the number of plants subjected to transformation) and transformation efficiency for the T1 generation (the number of transformed plants of T1 generation/(the number of plants of T1 generation subjected to the verification for incorporation of foreign genes into genomes).

According to the method of plant transformation of the present invention, transformation efficiency of 2% to 40%, and preferably 3% to 30% can be achieved, although transformation efficiency is not limited thereto.

In the present invention, a seed with a shoot having a length of 1 mm or less (e.g., 0.5 mm to 1 mm) can be inoculated at a wound site with an *Agrobacterium* under application of a plant growth-inhibiting hormone, and subjected to vacuum treatment, and co-cultured at 23° C. to 30° C. (preferably 28° C.), resulting in particularly high transformation efficiency. In this method, inoculation is more preferably carried out with the use of a bacterial solution also containing Tween 20 and acetosyringone.

The present invention also provides a medium for preparing *Agrobacterium* used for plant transformation comprising the above-mentioned plant growth-inhibiting hormone. The medium may comprise a surfactant such as Tween 20 and a phenol such as acetosyringone. The medium may comprise a component of a culture medium for *Agrobacterium* (e.g., LB medium), and it may comprise an antibiotic for killing *Agrobacterium* so as to select a transformant. Use of the medium is advantageous for preparation of a bacterial solution used when inoculating a plant with the *Agrobacterium*.

EXAMPLES

Hereafter, the present invention is described in greater detail with reference to the Examples, but the technical scope of the present invention is not limited to these Examples.

Example 1

Figure 1:
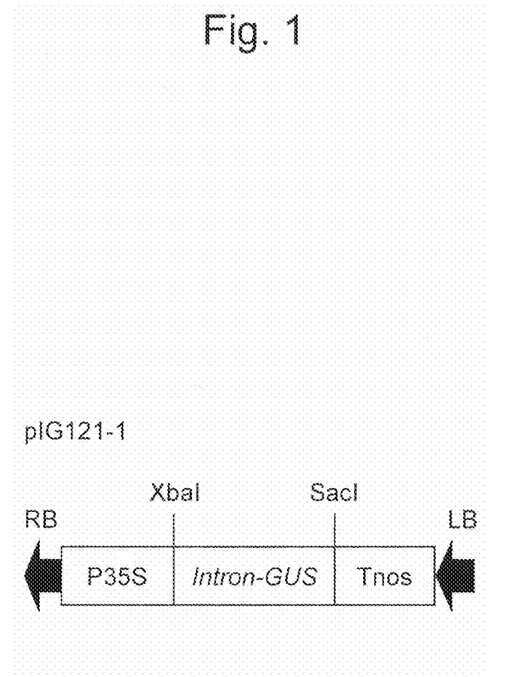
FIG. 1 shows a vector map of pIG121-1.

(1) Preparation of Foreign-Gene-Containing Vector for Gene Introduction into Plant The binary vector for gene introduction into plant, pIG121-Hm, (Ohta, S. et al., Plant Cell Physiol., 31, 805-813, 1990) was cleaved with restriction enzymes NheI and HindIII to remove the kanamycin resistance marker gene, NPTII, from the T-DNA region. Then, the vector was further cleaved with restriction enzymes EcoRI and StuI to remove the hygromycin resistance marker gene, HPT, from the T-DNA region, thereby preparing a pIG121-1 vector. FIG. 1 shows a vector map of it. All selectable marker genes other than the GUS gene were absent from the T-DNA region, in the pIG121-1 vector. As a foreign gene in the pIG121-1 vector to be introduced into a plant, the GUS (β-galactosidase) gene that was already contained in the T-DNA region of pIG121-Hm was used.

(2) Preparation of *Agrobacterium* Comprising pIG121-1 Introduced Thereinto

The binary vector pIG121-1 obtained in (1) above was introduced into *Agrobacterium tumefaciens* strain LBA4404 bacteria via freeze-thawing (Hofgen et al., 1998, Storage of competent cells for *Agrobacterium* transformation, Nucleic Acids Res., October 25; 16 (20): 9877) to transform the *Agrobacterium*. In order to select a transformed *Agrobacterium*, the *Agrobacterium* subjected to the gene introduction were grown on YEP medium containing 50 mg/l of kanamycin and 50 mg/l of streptomycin.

(3) Plant Transformation Using Abscisic Acid (1)

The *Agrobacterium* into which pIG121-1 had been introduced prepared above were cultured in LB medium containing kanamycin and streptomycin (50 mg/l each) at 28° C. for 18 hours to prepare an *Agrobacterium* solution. Through this culture, the transformed *Agrobacterium* carrying pIG121-1 were selected on the basis of functions of the kanamycin resistance gene and the streptomycin resistance gene existing outside the T-DNA region of pIG121-1.

Abscisic acid (final concentration: 100 µM) was added to the bacterial solution prepared in the manner described above, and the resulting bacterial solution was used below as an *Agrobacterium* solution for inoculation.

Pretreatment of seeds was carried out by soaking wheat seeds (variety: Yumechikara (Wheat Nourin 172)) in 70% ethanol for 5 minutes, followed by shaking in a 20% antiformin solution for 10 minutes. The seeds were washed with water to remove the antiformin solution, wrapped in moistened Kim towel, and then cultured at 25° C. for 36 to 40 hours for germination.

Subsequently, a portion around the shoot of the seed (shoot length: about 2 mm) was pierced with a needle (diameter: 0.71 mm) to a depth of about 1 mm to provide a pore. The seeds with thus wounded meristems were soaked in the *Agrobacterium* solution prepared above for about 20 minutes to inoculate the seeds with the *Agrobacterium*. Thereafter, the seeds were removed from the *Agrobacterium* solution, mounted on moistened Kim towel, and then cultured in a covered petri dish at 22° C. for 2 days (co-culture). Thus, the seeds were infected with *Agrobacterium*. Next, in order to disinfect *Agrobacterium*, the co-cultured seeds were soaked in an aqueous solution of cefotaxime (1,000 ppm) and then shaken at room temperature for 2 hours. Subsequently, the seeds were removed from the aqueous solution of cefotaxime, mounted on moistened Kim towel, and then grown in a covered petri dish at 25° C. for 2 days. The seeds were transferred to a pot containing culture soil and then grown at 25° C. under the long-day conditions (a light period of 16 hours and a dark period of 8 hours).

When the seeds grew to the 5- to 6-leaf stage, genome PCR was carried out to select transformants. PCR conditions are as shown in Table 1 below.

TABLE 1

| Step | ° C. | Duration | Number of cycles |
| --- | --- | --- | --- |
| 1 | 94 | 3 min | 1 |
| 2 | 94 | 30 sec | 35 |
| 3 | 57 | 30 sec | |
| 4 | 72 | 1 min | |
| 5 | 72 | 5 min | 1 |
| 6 | 4 | ∞ | |

The primers shown below were used for PCR.

```
                                   (SEQ ID NO: 1)
GUS 5':       5'-acctcgcattacccttacgc-3'

(SEQ ID NO: 2)
GUS 3':       5'-tatccacgccgtattcggtg-3'
```

Figure 2:
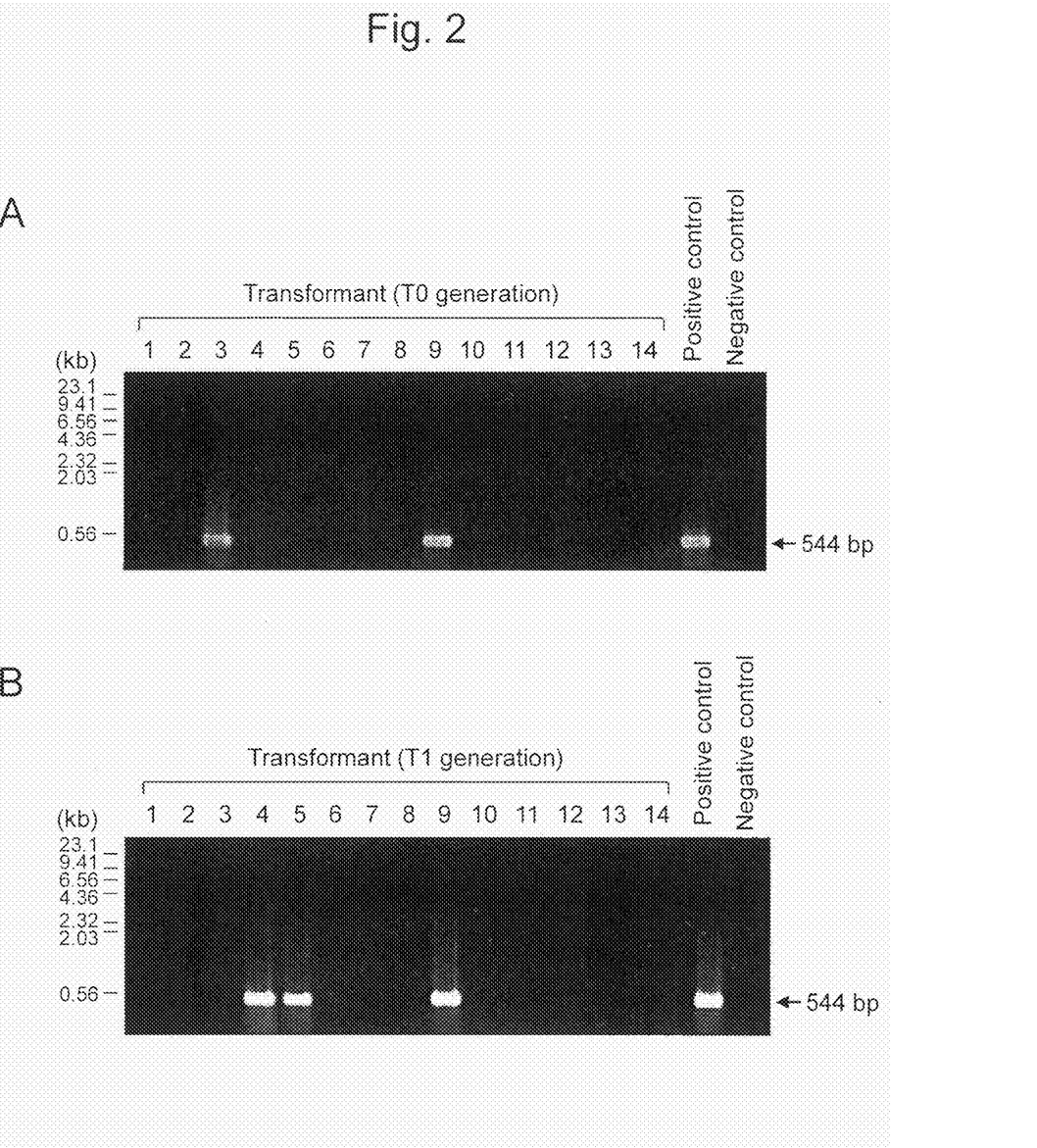
FIG. 2 shows an electrophoretic photograph showing results of PCR amplification performed for selecting a transformant.

FIG. 2A shows the results of electrophoresis of the resulting PCR product. A band of interest demonstrating the introduction of the GUS gene (544 bp) was detected in 2 of the 14 transformed individuals (T0 generation).

Considering that Yumechikara is an autumn wheat variety, the obtained transformants were subjected to vernalization at 4° C. for 1.5 months to facilitate flower bud formation. Subsequently, the transformants (T0 generation) were self-crossed to obtain T1 seeds, and gene introduction and gene expression in the T1 generation were verified.

Expression of the transgene in the T1 generation was verified via GUS staining. The GUS reaction solution having the composition shown in Table 2 below was used.

TABLE 2

| Composition of GUS reaction solution | |
| --- | --- |
| | Concentration |
| Phosphate buffer (pH 7.0) | 100 mM |
| $K_3Fe(CN)_6$ | 1.5 mM |
| $K_4Fe(CN)_6$ | 1.5 mM |
| Triton (Tween20) | 0.1% |
| X-Gluc | 0.5 mg/ml |

Figure 3:
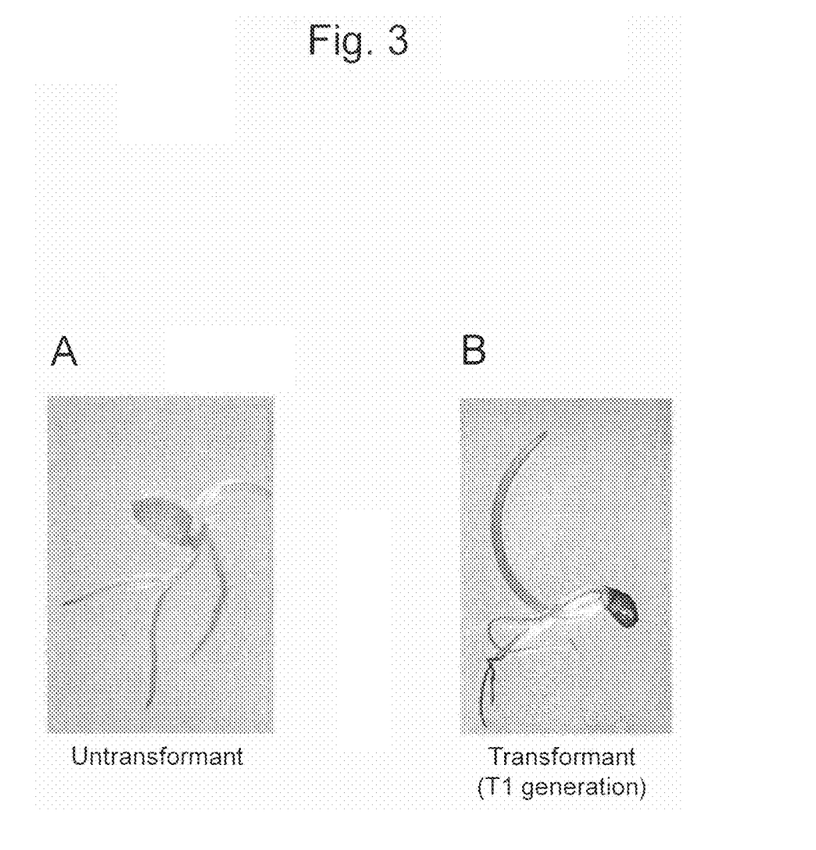
FIG. 3 shows a photograph showing the results of GUS staining that demonstrate the expression status of a transgene in a seedling of a transformant at the T1 generation and in a seedling of an untransformant (control).
Figure 4:
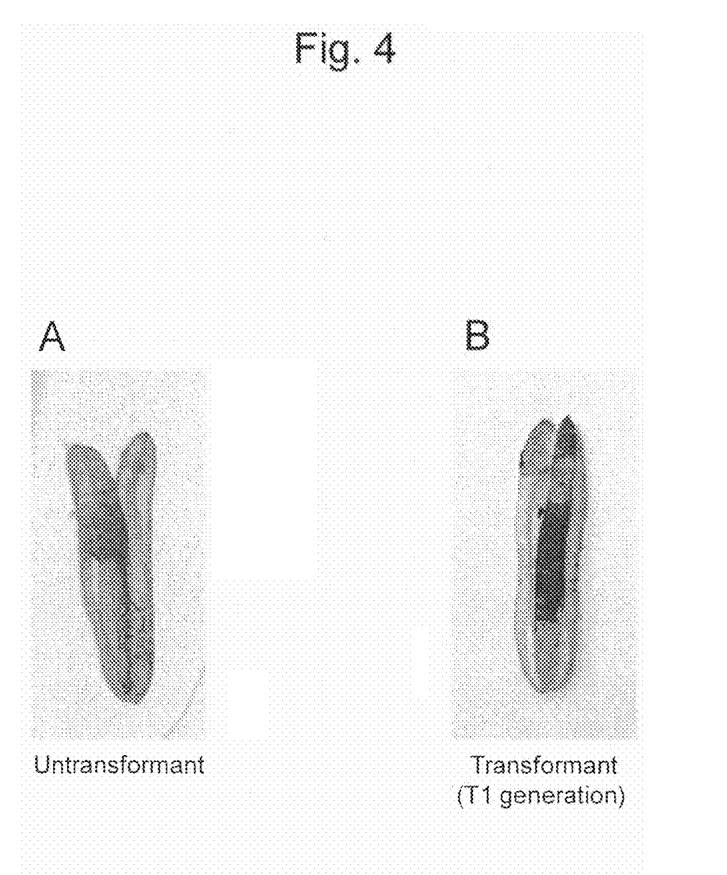
FIG. 4 shows a photograph showing the results of GUS staining that demonstrate the expression status of a transgene in an anther of a transformant at the T1 generation and in an anther of an untransformant (control).

An adequate amount of GUS reaction solution was added to the seedlings that had been cultured for 3 days or the anthers of the plants that had been cultured for about 1.5 months after the germination of T1 seeds, at 37° C. overnight for GUS reaction, and then the reaction solution was discarded, 70% ethanol was added to terminate the coloration reaction, and GUS activity was confirmed via observation of staining. As shown in FIG. 3B and FIG. 4B, GUS staining was observed in the seedlings and anthers of the plant individuals with expressing transgenes.

Gene introduction at the T1 generation was verified via genome PCR under the same conditions as with the case of the T0 generation. FIG. 2B shows the results of electrophoresis of the resulting PCR product. A band of interest was detected in 3 of the 14 individuals subjected to the genome PCR.

Transformation efficiency (T0 generation×T1 generation) achieved by the method of the present invention thus determined was 3.1% (=14.3% (T0)×21.4% (T1)).

Example 2

The *Agrobacterium* into which pIG121-1 had been introduced as prepared in Example 1 was cultured in LB medium containing kanamycin and streptomycin (50 mg/l each) at 28° C. for 18 hours to prepare an *Agrobacterium* solution.

Jasmonic acid (final concentration: 100 μM) was added to the bacterial solution prepared in the manner described above, and the resulting bacterial solution was used below as an *Agrobacterium* solution for inoculation.

Pretreatment of seeds was carried out by soaking wheat seeds (variety: Yumechikara) in 70% ethanol for 5 minutes, followed by shaking in a 20% antiformin solution for 10 minutes. The seeds were washed with water to remove the antiformin solution, wrapped in moistened Kim towel, and then cultured at 25° C. for 36 to 40 hours for germination.

Subsequently, a portion around the shoot of the seed (shoot length: about 2 mm) was pierced with a needle (diameter: 0.71 mm) to a depth of about 1 mm to provide a pore. The seeds with thus wound meristems were soaked in the *Agrobacterium* solution prepared above for about 20 minutes to inoculate the seeds with the *Agrobacterium*. Thereafter, the seeds were removed from the *Agrobacterium* solution, mounted on moistened Kim towel, and then cultured in a covered petri dish at 22° C. for 2 days (co-culture). Thus, the seeds were infected with *Agrobacterium*. Next, in order to disinfect *Agrobacterium*, the co-cultured seeds were soaked in an aqueous solution of cefotaxime (1,000 ppm) and then shaken at room temperature for 2 hours. Subsequently, the seeds were removed from the aqueous solution of cefotaxime, mounted on moistened Kim towel, and then grown in a covered petri dish at 25° C. for 2 days. The seeds were transferred to a pot containing culture soil and then grown under the same conditions as in Example 1.

When the seeds grew to the 5- to 6-leaf stage, genome PCR was carried out to select transformants. PCR conditions and primers used are as described in Example 1.

Considering that Yumechikara is an autumn wheat variety, the obtained transformants were subjected to vernalization at 4° C. for 1.5 months to facilitate flower bud formation. Subsequently, the transformants (T0 generation) were self-crossed to obtain T1 seeds, and gene introduction and gene expression in the T1 generation were verified in the same manner as in Example 1.

Transformation efficiency (T0 generation×T1 generation) achieved by the method of the present invention thus determined was 2.4%.

Example 3

The *Agrobacterium* into which pIG121-1 had been introduced as prepared in Example 1 was cultured in LB medium containing kanamycin and streptomycin (50 mg/l each) at 28° C. for 18 hours to prepare an *Agrobacterium* solution.

Abscisic acid (final concentration: 100 μM) and Tween 20 (final concentration: 0.1%) were added to the bacterial solution prepared in the manner described above, and the resulting bacterial solution was used below as an *Agrobacterium* solution for inoculation.

Pretreatment of seeds was carried out by soaking wheat seeds (variety: Yumechikara) in 70% ethanol for 5 minutes, followed by shaking in a 20% antiformin solution for 10 minutes. The seeds were washed with water to remove the antiformin solution, wrapped in moistened Kim towel, and then cultured at 25° C. for 36 to 40 hours for germination.

Subsequently, a portion around the shoot of the seed (shoot length: 1 mm or less, about 0.5 to 1.0 mm) was pierced with a needle (diameter: 0.71 mm) to a depth of about 1 mm to provide a pore. The seeds with thus wound meristems were soaked in the *Agrobacterium* solution prepared above, and vacuum treatment was carried out using an aspirator for 20 minutes to inoculate the seeds with the *Agrobacterium*. Thereafter, the seeds were removed from the *Agrobacterium* solution, mounted on moistened Kim towel, and then cultured in a covered petri dish at 28° C. for 2 days (co-culture). Thus, the seeds were infected with *Agrobacterium*. Next, in order to disinfect *Agrobacterium*, the co-cultured seeds were soaked in an aqueous solution of cefotaxime (1,000 ppm) and then shaken at room temperature for 2 hours. Subsequently, the seeds were removed from the aqueous solution of cefotaxime, mounted on moistened Kim towel, and then grown in a covered petri dish at 25° C. for 2 days. The seeds were transferred to a pot containing culture soil and then grown under the same conditions as in Example 1.

When the seeds grew to the 5- to 6-leaf stage, genome PCR was carried out to select transformants. PCR conditions and primers used are as described in Example 1.

Considering that Yumechikara is an autumn wheat variety, the obtained transformants were subjected to vernalization at 4° C. for 1.5 months to facilitate flower bud formation. Subsequently, the transformants (T0 generation) were self-crossed to obtain T1 seeds, and gene introduction and gene expression in the T1 generation were verified in the same manner as in Example 1.

Transformation efficiency (T0 generation×T1 generation) achieved by the method of the present invention thus determined was 5.1%.

Example 4

The *Agrobacterium* into which pIG121-1 had been introduced as prepared in Example 1 was cultured in LB medium containing kanamycin and streptomycin (50 mg/1 each) at 28° C. for 18 hours to prepare an *Agrobacterium* solution.

Abscisic acid (final concentration: 100 μM), Tween 20 (final concentration: 0.1%), and acetosyringone (100 μM) were added to the bacterial solution prepared in the manner described above, and the resulting bacterial solution was used below as an *Agrobacterium* solution for inoculation.

Pretreatment of seeds was carried out by soaking wheat seeds (variety: Yumechikara) in 70% ethanol for 5 minutes, followed by shaking in a 20% antiformin solution for 10 minutes. The seeds were washed with water to remove the antiformin solution, wrapped in moistened Kim towel, and then cultured at 25° C. for 36 to 40 hours for germination.

Subsequently, a portion around the shoot of the seed (shoot length: 1 mm or less, about 0.5 to 1.0 mm) was pierced with a needle (diameter: 0.71 mm) to a depth of about 1 mm to provide a pore. The seeds with thus wound meristems were soaked in the *Agrobacterium* solution prepared above for about 20 minutes, and vacuum treatment was carried out using an aspirator for 20 minutes to inoculate the seeds with the *Agrobacterium*. Thereafter, the seeds were removed from the *Agrobacterium* solution, mounted on moistened Kim towel, and then cultured in a covered petri dish at 28° C. for 2 days (co-culture). Thus, the seeds were infected with *Agrobacterium*. Next, in order to disinfect *Agrobacterium*, the co-cultured seeds were soaked in an aqueous solution of cefotaxime (1,000 ppm) and then shaken at room temperature for 2 hours. Subsequently, the seeds were removed from the aqueous solution of cefotaxime, mounted on moistened Kim towel, and then grown in a covered petri dish at 25° C. for 2 days. The seeds were transferred to a pot containing culture soil and then grown under the same conditions as in Example 1.

When the seeds grew to the 5- to 6-leaf stage, genome PCR was carried out to select transformants. PCR conditions and primers used are as described in Example 1.

Considering that Yumechikara is an autumn wheat variety, the obtained transformants were subjected to vernalization at 4° C. for 1.5 months to facilitate flower bud formation. Subsequently, the transformants (T0 generation) were self-crossed to obtain T1 seeds, and gene introduction and gene expression in the T1 generation were verified in the same manner as in Example 1.

Transformation efficiency (T0 generation×T1 generation) achieved by the method of the present invention thus determined was 7.2%.

Example 5

In the same manner as in Example 4, except that a wheat variety, Haruyokoi (variety registration number 8834, one spring wheat variety), was used. the genes were introduced into wheat seeds and T1 seeds were obtained. Thereafter, gene introduction and gene expression in the T1 generation were verified as described in Example 1.

Transformation efficiency (T0 generation×T1 generation) achieved by the method of the present invention thus determined was 10.2%.

Example 6

The genes were introduced into wheat seeds and T1 seeds were obtained in the same manner as in Example 4, except that 300 μM abscisic acid was added. Thereafter, gene introduction and gene expression in the T1 generation were verified in the same manner as described in Example 1.

Transformation efficiency (T0 generation×T1 generation) achieved by the method of the present invention thus determined was 7.0%.

Example 7

The genes were introduced into wheat seeds and T1 seeds were obtained in the same manner as in Example 4, except that 10 μM abscisic acid was added. Thereafter, gene introduction and gene expression in the T1 generation were verified in the same manner as described in Example 1.

Transformation efficiency (T0 generation×T1 generation) achieved by the method of the present invention thus determined was 6.3%.

Example 8

Plant transformation was carried out in the same manner as in Example 1, except that a variety "Toyomusume" of soybeans was used and axillary buds of the plants 14 days after germination were inoculated with *Agrobacterium*, and then gene introduction and gene expression in the T0 generation were verified.

Transformation efficiency (T0 generation) achieved by the method of the present invention thus determined was 30%.

Example 9

Plant transformation was carried out in the same manner as in Example 8, except that the *Agrobacterium tumefaciens* M21 mutant was used, and then gene introduction in the T0 generation was verified.

Figure 5:
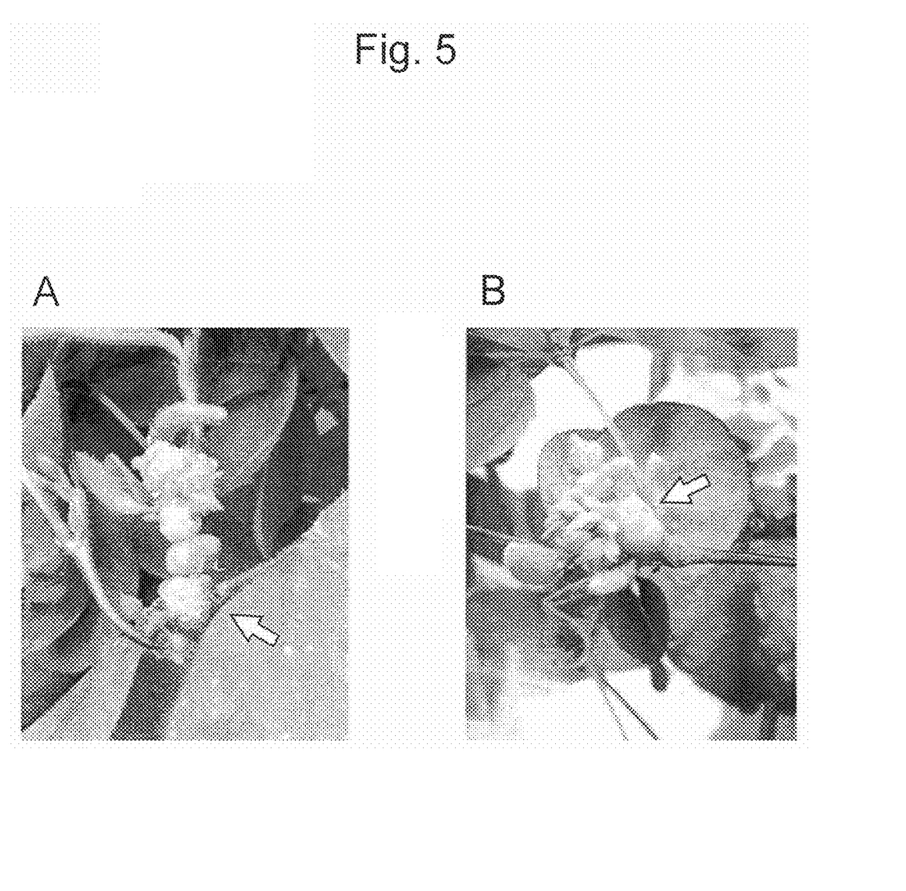
FIG. 5 shows a photograph showing a tumor formed in a transformed soybean plant (T0 generation) obtained via transformation with an *Agrobacterium* M21 mutant (FIGS. 5A and B).

The *Agrobacterium tumefaciens* M21 mutant (hereafter referred to as "the M21 mutant") was obtained via mutation of the *Agrobacterium tumefaciens* A208 strain (C58 chromosome, nopaline T37 pTi) with the use of transposon 5 (Tn5) (Majumder, P. et al., J. Biosci. Bioeng., 90: 328-331, 2000; WO 2005/024034). In the M21 mutant, Tn5 is inserted into the tryptophan monooxygenase gene involved in biosynthesis of indoleacetic acid (IAA) in the T-DNA region of the Ti plasmid. This would cause hormone imbalance in plants transformed via infection with the M21 mutant, which would lead to phenotypic changes. The soybean plants transformed with the M21 mutant underwent tumorigenesis, as shown in FIG. 5A and FIG. 5B. Thus, the presence or absence of the transformation was easily determined via visual inspection.

In planta transformation efficiency in soybeans using the *Agrobacterium tumefaciens* M21 mutant is shown in Table 3 below. Transformation efficiency (T0 generation) achieved by the method of the present invention was 75%.

TABLE 3

| Number of plants subjected to transformation | Number of transformed plants | Number of untransformed plants |
|---|---|---|
| 12 | 9 (75%) | 3 (25%) |

Example 10

Seeds of maize (*Zea mays*) were washed with sterile water 2 or 3 times to wash the red disinfectant away from the seed coat. The washed seeds were soaked in sterile water and incubated at 25° C. for 2 days. Water was exchanged with fresh water once during incubation. Thus, the seeds absorbed water and the embryonic portions became white. These seeds were used for the experiment described below. A bacterial solution containing pIG121-1-carrying *Agrobacterium* and abscisic acid (final concentration: 100 µM) was prepared as an *Agrobacterium* solution for inoculation in the same manner as in Example 1.

With the use of a needle (φ 0.71 mm), the shoot (length: 1 mm) of the embryo (longer diameter: about 1 cm) of the maize seed was pierced 4 times on the apex, in which the meristem was considered to be present, to a depth of 0.5 mm to 1 mm to provide 4 pores in an area of about 2 mm square. Thereafter, the *Agrobacterium* solution for inoculation prepared above was applied dropwise to the pores using a pipette to inoculate the seeds with *Agrobacterium*.

Subsequently, a filter paper was placed in a petri dish and moistened with water. The maize seeds inoculated with *Agrobacterium* were placed on the filter paper and the petri dish was covered. The petri dish was then placed in an incubator at 25° C., and incubation was carried out in the dark for 2 days. After co-culture was conducted for 2 days, the seeds were sowed in culture soil and grown.

Figure 6:
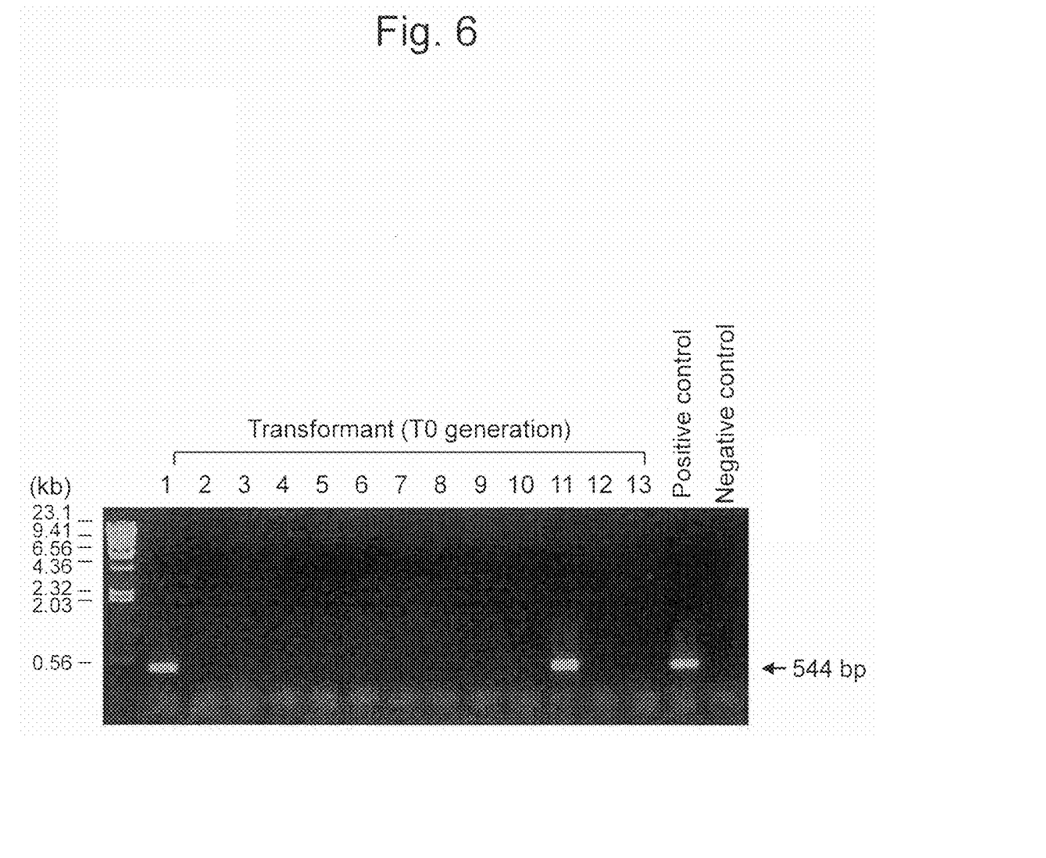
FIG. 6 shows an electrophoretic photograph demonstrating the results of PCR amplification performed for selecting a transformant. It shows results for maize individual plants at the T0 generation.

Gene introduction in the T0 generation was verified in the same manner as in Example 1. Plants (5-leaf stage) 20 days after transformation were used for genomic PCR. FIG. 6 shows an electrophoretic photograph demonstrating the results of PCR amplification. A 544-bp PCR product indicating GUS gene introduction was detected in 2 plants. In planta transformation efficiency for maize using pIG121-1-carrying *Agrobacterium* is shown in Table 4 below. Transformation efficiency (T0 generation) achieved by the method of the present invention was 15.4%.

TABLE 4

| Number of plants subjected to transformation | Number of transformed plants | Number of untransformed plants |
|---|---|---|
| 13 | 2 (15.4%) | 11 (84.6%) |

Comparative Example 1

The *Agrobacterium* strains into which pIG121-1 had been introduced prepared in Example 1 were cultured in LB medium containing kanamycin and streptomycin (50 mg/l each) at 28° C. for 18 hours to prepare an *Agrobacterium* solution.

The bacterial solution prepared in the manner described above was used below as an *Agrobacterium* solution for inoculation. No plant growth-inhibiting hormone was added to this bacterial solution.

Pretreatment of seeds was carried out by soaking wheat seeds (variety: Yumechikara) in 70% ethanol for 5 minutes, followed by shaking in a 20% antiformin solution for 10 minutes. The seeds were washed with water to remove the antiformin solution, wrapped in moistened Kim towel, and then cultured at 25° C. for 36 to 40 hours for germination.

With the use of a needle (φ 0.71 mm), subsequently, a portion around the shoot of the seed (shoot length: about 2 mm) was pierced to a depth of about 1 mm to provide a pore. The seeds with thus wound meristems were soaked in the *Agrobacterium* solution prepared above for about 20 minutes to inoculate the seeds with the *Agrobacterium*. Thereafter, the seeds were removed from the *Agrobacterium* solution, mounted on moistened Kim towel, and then cultured in a covered petri dish at 22° C. for 2 days (co-culture). Thus, the seeds were infected with *Agrobacterium*. Next, in order to disinfect *Agrobacterium*, the co-cultured seeds were soaked in an aqueous solution of cefotaxime (1,000 ppm) and then shaken at room temperature for 2 hours. Subsequently, the seeds were removed from the aqueous solution of cefotaxime, mounted on moistened Kim towel, and then grown in a covered petri dish at 25° C. for 2 days. The seeds were transferred to a pot containing culture soil and then grown under the same conditions as in Example 1.

When the seeds grew to the 5- to 6-leaf stage, genome PCR was carried out to select transformants. PCR conditions and primers used are as described in Example 1.

Considering that Yumechikara is an autumn wheat variety, the obtained transformants were subjected to vernalization at 4° C. for 1.5 months to accelerate flower bud formation. Subsequently, the transformants (T0 generation) were self-crossed to obtain T1 seeds, and gene introduction and gene expression in the T1 generation were verified in the same manner as in Example 1.

Plant transformation efficiency (T0 generation×T1 generation) thus determined was 1.0%.

Comparative Example 2

The experiment was carried out in the same manner as in Comparative Example 1, except that co-culture was carried out by removing seeds from the *Agrobacterium* solution, mounting the seeds on moistened Kim towel, and performing culture in a covered petri dish at 28° C. for 2 days (co-culture).

Plant transformation efficiency (T0 generation×T1 generation) thus determined was 3.6%.

Comparative Example 3

The experiment was carried out in the same manner as in Comparative Example 1, except that seeds with the wound meristems were soaked in the same *Agrobacterium* solution as used in Comparative Example 1 and vacuum treatment was carried out using an aspirator for 20 minutes (i.e., via reduced-pressure infiltration) to inoculate the seeds with *Agrobacterium* in the step of *Agrobacterium* infection.

Plant transformation efficiency (T0 generation×T1 generation) thus determined was 2.4%.

Comparative Example 4

The experiment was carried out in the same manner as in Comparative Example 1, except that a portion around the shoot of the seed (shoot length: 1 mm or less, about 0.5 to 1.0 mm) was pierced with a needle (diameter: 0.71 mm) to a depth of about 1 mm to provide a pore in the step of *Agrobacterium* infection.

Plant transformation efficiency (T0 generation×T1 generation) thus determined was 2.5%.

Comparative Example 5

Plant transformation was carried out in the same manner as in Comparative Example 1, except that a variety "Toyomusume" of soybeans was used and axillary buds of the plants 14 days after germination were inoculated with *Agrobacterium*, and then gene introduction and gene expression in the T0 generation were verified.

Transformation efficiency (T0 generation) achieved by the method of the present invention thus determined was 10%.

Comparative Example 6

Plant transformation was carried out in the same manner as in Example 9, except that abscisic acid was not added to the *Agrobacterium* solution, and then gene introduction in the T0 generation was verified. Transformation efficiency (T0 generation) achieved by the method of the present invention thus determined was 30%.

Comparative Example 7

Plant transformation was carried out in the same manner as in Example 10, except that abscisic acid was not added to the *Agrobacterium* solution, and then gene introduction and gene expression in the T0 generation were verified. Transformation efficiency (T0 generation) achieved by the method of the present invention thus determined was 0%.

INDUSTRIAL APPLICABILITY

The method of transformation of the present invention can be used for carrying out plant transformation with high efficiency and efficiently producing transformed plants of interest. The method of the present invention facilitates transformation of wider plant varieties.

Sequence Listing Free Text

SEQ ID NOs: 1 and 2: Primers

All publications, patents, and patent applications cited herein are incorporated herein by reference in their entirety.

The invention claimed is:

1. A method of transforming a plant, comprising inoculating an *Agrobacterium* solution comprising a plant growth-inhibiting hormone at a final concentration of from 10 to 100 µM and an *Agrobacterium* carrying a vector comprising a foreign gene into a wound site of a shoot apical meristem of a germinated seed having a shoot that has a length of 1 mm or less, and infecting the shoot apical meristem with the *Agrobacterium*, wherein the plant growth-inhibiting hormone is abscisic acid or jasmonic acid, and the seed is of a Poaceae or Leguminosae plant.

2. The method according to claim 1, further comprising subjecting the seed inoculated with the *Agrobacterium* solution to vacuum treatment and/or co-culture.

3. The method according to claim 1, wherein the vector comprises a T-DNA region in which a foreign gene is contained but no selectable marker gene is contained.

* * * * *